(12) United States Patent
Denniston, V

(10) Patent No.: US 11,134,710 B2
(45) Date of Patent: *Oct. 5, 2021

(54) CANNABINOID EMULSION PRODUCT AND PROCESS FOR MAKING THE SAME

(71) Applicant: Aceso Wellness LLC, Denver, CO (US)

(72) Inventor: Joseph Faries Denniston, V, Wheat Ridge, CO (US)

(73) Assignee: Aceso Wellness LLC, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/656,313

(22) Filed: Oct. 17, 2019

(65) Prior Publication Data

US 2020/0046007 A1 Feb. 13, 2020

Related U.S. Application Data

(63) Continuation of application No. 15/462,495, filed on Mar. 17, 2017, now Pat. No. 10,542,770.

(Continued)

(51) Int. Cl.

| | |
|---|---|
| *A23L 33/16* | (2016.01) |
| *A61K 9/46* | (2006.01) |
| *A61K 31/198* | (2006.01) |
| *A61K 31/519* | (2006.01) |
| *A61K 36/53* | (2006.01) |
| *A61K 36/185* | (2006.01) |
| *A61K 38/48* | (2006.01) |
| *A23L 2/40* | (2006.01) |
| *A23L 2/52* | (2006.01) |
| *A23L 33/155* | (2016.01) |
| *A23L 33/15* | (2016.01) |
| *A23L 33/115* | (2016.01) |
| *A61K 31/51* | (2006.01) |
| *A61K 36/73* | (2006.01) |
| *A61K 31/593* | (2006.01) |
| *A61K 31/714* | (2006.01) |
| *A61K 36/752* | (2006.01) |
| *A61K 31/4188* | (2006.01) |
| *A61K 9/20* | (2006.01) |

(Continued)

(52) U.S. Cl.
CPC ............... *A23L 33/16* (2016.08); *A23L 2/395* (2013.01); *A23L 2/40* (2013.01); *A23L 2/52* (2013.01); *A23L 33/115* (2016.08); *A23L 33/15* (2016.08); *A23L 33/155* (2016.08); *A61K 9/0007* (2013.01); *A61K 9/2009* (2013.01); *A61K 31/07* (2013.01); *A61K 31/191* (2013.01); *A61K 31/198* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/593* (2013.01); *A61K 31/7008* (2013.01); *A61K 31/714* (2013.01); *A61K 36/185* (2013.01); *A61K 36/53* (2013.01); *A61K 36/73* (2013.01); *A61K 36/752* (2013.01); *A61K 36/81* (2013.01); *A61K 36/9066* (2013.01); *A61K 38/4873* (2013.01); *C12Y 304/22004* (2013.01); *C12Y 304/22032* (2013.01); *C12Y 304/22033* (2013.01); *A23V 2002/00* (2013.01); *A23V 2200/31* (2013.01)

(58) Field of Classification Search
CPC ........ A23L 33/16; A23L 33/115; A23L 33/15; A23L 33/155; A23L 2/395; A23L 2/40; A23L 2/52; A61K 9/0007; A61K 9/2009; A61K 31/07; A61K 31/191; A61K 31/198; A61K 31/4188; A61K 31/4415; A61K 31/455; A61K 31/51; A61K 31/519; A61K 31/525; A61K 31/593; A61K 31/7008; A61K 31/714; A61K 36/185; A61K 36/53; A61K 36/73; A61K 36/752; A61K 36/81; A61K 36/9066; A61K 38/487

See application file for complete search history.

(56) References Cited

U.S. PATENT DOCUMENTS

| | | |
|---|---|---|
| 3,077,405 A | 2/1963 | Clinton et al. |
| 3,908,024 A | 9/1975 | Wankier |

(Continued)

FOREIGN PATENT DOCUMENTS

| | | |
|---|---|---|
| AU | 2013234830 A1 | 11/2014 |
| CA | 2931486 A1 | 5/2015 |

(Continued)

OTHER PUBLICATIONS

Tcherkasskaya, Olga V., "Advisory Action Regarding U.S. Appl. No. 15/462,495", filed Apr. 27, 2018, p. 18, Published in: US.

(Continued)

*Primary Examiner* — Robert A Wax
*Assistant Examiner* — Olga V. Tcherkasskaya
(74) *Attorney, Agent, or Firm* — Neugeboren O'Dowd PC

(57) ABSTRACT

A dry consumable preparation and related methods are disclosed. The preparation has a bulking agent, and a cannabinoid and/or a cannabinoid extract containing one or more cannabinoids plated onto the bulking agent. The preparation also has an effervescence agent. The effervescence agent has sodium bicarbonate, potassium bicarbonate, and at least one acid, the at least one acid having at least one of citric acid, tartaric acid, or malic acid. The effervescence agent further has a ratio of sodium bicarbonate to potassium bicarbonate to the acid(s) that creates a chemical pH buffering system at a targeted pH range when the dry consumable preparation is added to a targeted amount of water.

13 Claims, 7 Drawing Sheets

Related U.S. Application Data

(60) Provisional application No. 62/310,079, filed on Mar. 18, 2016.

(51) Int. Cl.

| | |
|---|---|
| *A61K 36/9066* | (2006.01) |
| *A61K 31/455* | (2006.01) |
| *A61K 31/07* | (2006.01) |
| *A61K 31/4415* | (2006.01) |
| *A61K 31/525* | (2006.01) |
| *A61K 31/191* | (2006.01) |
| *A61K 31/7008* | (2006.01) |
| *A23L 2/395* | (2006.01) |
| *A61K 36/81* | (2006.01) |

(56) References Cited

U.S. PATENT DOCUMENTS

| | | |
|---|---|---|
| 8,808,734 B2 | 8/2014 | Winnicki |
| 9,474,725 B1 | 10/2016 | Reillo et al. |
| 2003/0229027 A1 | 12/2003 | Eissens et al. |
| 2007/0072939 A1 | 3/2007 | Kupper |
| 2007/0116829 A1 | 5/2007 | Prakash et al. |
| 2008/0112895 A1 | 5/2008 | Kottayil et al. |
| 2012/0231083 A1 | 9/2012 | Carley et al. |
| 2013/0184354 A1 | 7/2013 | Jackson et al. |
| 2013/0309291 A1 | 11/2013 | Stoll |
| 2014/0234488 A1 | 8/2014 | Chang |
| 2014/0302148 A1 | 10/2014 | Winnicki |
| 2015/0079235 A1 | 3/2015 | Wright et al. |
| 2015/0110924 A1 | 4/2015 | Bromley |
| 2016/0051480 A1 | 2/2016 | Taha |
| 2016/0081976 A1 | 3/2016 | Bromley |
| 2016/0129060 A1 | 5/2016 | Bray et al. |
| 2016/0166498 A1 | 6/2016 | Anastassov et al. |
| 2016/0220593 A1 | 8/2016 | Anastassov et al. |
| 2016/0279073 A1 | 9/2016 | Donsky et al. |
| 2016/0324776 A1 | 11/2016 | Glatzel |
| 2016/0367522 A1 | 12/2016 | De Vries et al. |

FOREIGN PATENT DOCUMENTS

| | | |
|---|---|---|
| EP | D175788 A1 | 4/1986 |
| EP | 2421384 A1 | 2/2012 |
| EP | 2968259 A1 | 1/2016 |
| EP | 3062774 A2 | 9/2016 |
| WO | 2009016091 A1 | 2/2009 |
| WO | 2011000524 A1 | 1/2011 |
| WO | 2014206956 A1 | 12/2014 |
| WO | 2015025312 A1 | 2/2015 |
| WO | 2015068052 A2 | 5/2015 |
| WO | 2016147186 A1 | 9/2016 |

OTHER PUBLICATIONS

Tcherkasskaya, Olga V., "Final Office Action Re U.S. Appl. No. 15/462,495", filed Feb. 8, 2018, p. 20, Published in: US.

Tcherkasskaya, Olga V., "Final Office Action Re U.S. Appl. No. 15/462,495", filed Jul. 8, 2019, p. 10, Published in: US.

Tcherkasskaya, Olga V., "Office Action Re U.S. Appl. No. 15/462,495", filed Jan. 4, 2019, p. 18, Published in: US.

Percival, Shane, "Response to Office Action Re U.S. Appl. No. 15/462,495", filed Apr. 11, 2019, p. 19, Published in: US.

Percival, Shane, "Response to Office Action Re U.S. Appl. No. 15/462,495", filed May 22, 2018, p. 20, Published in: US.

Percival, Shane, "Response to Office Action Re U.S. Appl. No. 15/462,495", filed Aug. 26, 2019, p. 11, Published in: US.

Schneider, Laura, "Response to Office Action Re U.S. Appl. No. 15/462,495", filed Nov. 13, 2017, p. 14, Published in: US.

Tcherkasskaya, Olga V., "Office Action Regarding U.S. Appl. No. 15/462,495", filed Aug. 11, 2017, p. 13, Published in: US.

Rowe, David, "Chemistry and Technology of Flavours and Frangrances", 2005, p. 351, Publisher: Blackwell Publishing Ltd, Published in: Oxford, UK.

Domian et al., "Flowability and Homogeneity of Food Powders With Plated Oil Ingredient", "Journal of Food Process Engineering", Sep. 10, 2013, p. 2, vol. 36, No. 5.

| Table 1: Dry Preparation for Calming - 1000 | | | | | |
|---|---|---|---|---|---|
| | Embodiment 1 | Embodiment 2 | Embodiment 3 | Embodiment 3 | |
| Ingredient | Weight (g) | Weight (%) | Weight (g) | Weight (%) | |
| Sodium Citrate | 3-10 | 0.03-0.05 | 3.70 | 0.0493 | |
| Vitamin C | 20-100 | 0.2-0.5 | 22.50 | 0.3000 | |
| Coenzyme Q10 | 20-50 | 0.2-0.5 | 24.90 | 0.3320 | |
| Magna Sweet | 5-10 | 0.05-0.2 | 8.50 | 0.1133 | |
| L Theanine | 20-50 | 0.2-0.5 | 24.80 | 0.3306 | |
| Passionflower Flavor Powder | 10-20 | 0.1-0.3 | 15.00 | 0.2000 | |
| CBD Oil (64.5% CBD) | 10-12 | 0.05-0.25 | 11.60 | 0.1547 | |
| Fructose | 4000-6000 | 70-80 | 5703.00 | 76.0355 | |
| Grapefruit Oil | 25-50 | 0.3-0.5 | 32.20 | 0.4293 | |
| Lavender Oil (15:1 grapefruit oil:lavender oil) | 1-4 | 0.02-0.04 | 2.20 | 0.0293 | |
| Citric Acid | 1300-1400 | 17-19 | 1327.50 | 17.6990 | |
| Sodium Bicarbonate | 60-120 | 0.7-1.0 | 66.40 | 0.8853 | |
| Calcium Carbonate | 60-240 | 0.8-1.3 | 79.70 | 1.0626 | |
| Potassium Bicarbonate | 120-360 | 2.0-2.8 | 172.64 | 2.3017 | |
| Quillaja | 2.5-12 | 0.05-0.15 | 5.80 | 0.0773 | |
| Total: | | | 7500.44 | 100.00 | |

FIG. 1

Table 2: Dry Preparation for Wellness - 2000

| Ingredient | Embodiment 1 Weight (g) | Embodiment 2 Weight (%) | Embodiment 3 Weight (g) | Embodiment 3 Weight (%) |
|---|---|---|---|---|
| Vitamin A | 0.1-0.3 | 0.001-0.003 | 0.2 | 0.0027 |
| Vitamin D3 | 0.0075 - 0.030 | 0.0001-0.0003 | 0.015 | 0.0002 |
| Vitamin B6 | 4-5 | 0.004-0.008 | 0.45 | 0.0060 |
| Vitamin B3 | 3-5 | 0.03-0.07 | 3.6 | 0.0480 |
| Vitamin B2 | 1-2 | 0.005-0.03 | 1.3 | 0.0173 |
| Vitamin B1 | 1-2 | 0.005-0.03 | 1.3 | 0.0173 |
| Vitamin B12 | 0.04-0.05 | 0.0004-0.0008 | 0.046 | 0.0006 |
| Vitamin C | 20-100 | 0.1-0.5 | 22.5 | 0.30 |
| Zinc Gluconate | 1-2 | 0.01-0.04 | 1.8 | 0.0240 |
| Biotin | 0.05-0.2 | 0.0005-0.003 | 0.1 | 0.0013 |
| Malic Acid | 40-45 | 0.3-0.7 | 42.8 | 0.57 |
| Sodium Citrate | 3-10 | 0.05-0.2 | 8.5 | 0.11 |
| Honey Powder | 5-25 | 0.04-0.09 | 5.6 | 0.07 |
| Magna Sweet | 5-20 | 0.05-0.3 | 10.6 | 0.14 |
| Green Tea Flavor Powder | 1-30 | 0.1-0.3 | 15.00 | 0.20 |
| CBD Oil | 10-12 | 0.05-0.3 | 11.60 | 0.15 |
| Quillaja | 2.9-11.6 | 0.005-0.2 | 5.80 | 0.08 |
| Lemon Oil | 10-50 | 0.2-0.6 | 35.40 | 0.47 |
| Orange Oil | 5-100 | 0.2-0.5 | 26.80 | 0.36 |
| Cayenne Extract | 1-50 | 0.05-0.3 | 11.90 | 0.16 |
| Fructose | 5495-5523 | 68-79 | 5517.00 | 73.62 |
| Sodium Bicarbonate | 60-120 | 1.0-2.0 | 117.40 | 1.57 |
| Calcium Carbonate | 30-120 | 0.5-1.5 | 81.00 | 1.08 |
| Potassium Bicarbonate | 90-360 | 2.5-3.5 | 234.80 | 3.13 |
| Citric Acid | 1000-2000 | 16.5-18.5 | 1338.10 | 17.86 |
| Total: | | | 7493.61 | 100.0035 |

FIG. 2

Table 3: Dry Preparation for Soothing - 3000

| Ingredient | Embodiment 1 Weight (g) | Embodiment 2 Weight (%) | Embodiment 3 Weight (g) | Embodiment 3 Weight (%) |
|---|---|---|---|---|
| Sodium Citrate | 3-10 | 0.5-1.5 | 8.8 | 0.12 |
| Vitamin C | 20-100 | 0.2-0.4 | 22.5 | 0.30 |
| Cherry Flavor Powder | 5-25 | 0.1-0.3 | 15 | 0.20 |
| CBD Oil | | 0.05-0.2 | 11.6 | 0.15 |
| Glucosamine Sulfate | 10-200 | 0.9-2.0 | 99.9 | 1.33 |
| Vitamin D | 0.0075 - 0.03 | 0.0001-0.0005 | 0.02 | 0.0003 |
| Bromelain | 1-20 | 0.05-0.2 | 10.1 | 0.13 |
| Quillaja | 2.9-11.6 | 0.05-0.09 | 5.8 | 0.08 |
| Magna Sweet | 5-20 | 0.07-0.15 | 6.9 | 0.09 |
| Fructose G | 5850-5900 | 75-80 | 5870 | 78.37 |
| Cinnamon Oil | 5-50 | 0.1-0.4 | 21.2 | 0.28 |
| Turmeric Extract | 10-100 | 0.5-1.2 | 57.4 | 0.77 |
| Citric Acid | 1000-2000 | 13-16 | 1069.1 | 14.27 |
| Sodium Bicarbonate | 60-120 | 0.8-1.5 | 89.1 | 1.19 |
| Calcium Carbonate | 30-120 | 0.5-1.3 | 64.1 | 0.86 |
| Potassium Bicarbonate | 60-240 | 1.4-2.5 | 138.9 | 1.85 |
| Total: | | | 7490.42 | 100.00 |

FIG. 3

Table 4: Dry Preparation for Wellness - 4000

| Ingredient | Embodiment 1 Weight (mg) | Embodiment 2 Weight (%) | Embodiment 3 Weight (mg) | Embodiment 3 Weight (%) |
|---|---|---|---|---|
| Biotin (Vitamin B7) | 0.05-0.02 | .0005-.002 | 0.08 | 0.001 |
| Vitamin A Palmitate | 0.1-0.3 | .002-.004 | 0.24 | 0.003 |
| Vitamin B1 (Thiamine HCL) | 1-2 | .015-.03 | 1.35 | 0.02 |
| Vitamin B2 (Riboflavin) | 1-2 | .015-.03 | 1.35 | 0.02 |
| Vitamin B3 (Niacin USP) | 3-5 | .04-.06 | 3.6 | 0.05 |
| Vitamin B6 (Pyridoxine HCL) | 4-5 | .05-.07 | 4.5 | 0.06 |
| Vitamin B12 (Cyanocobalamin) | 0.04-0.06 | .0005-.003 | 0.05 | 0.001 |
| Vitamin C (Ascorbic Acid) | 200-1000 | 2-20 | 750 | 9.94 |
| Vitamin D3 (Cholecalciferol) | 0.0075-0.03 | .00005-.0002 | 0.01 | 0.0001 |
| Zinc Gluconate | 1-3 | .015-.03 | 1.8 | 0.02 |
| Total: Vitamin Mix | | | 762.98 | |
| Sodium Bicarbonate | 250-1200 | 2-15 | 400 | 5.30 |
| Potassium Bicarbonate | 125-600 | 1-8 | 100 | 1.33 |
| Citric Acid | 300-1000 | 5-10 | 600 | 7.95 |
| Tartaric Acid | 300-1000 | 4-10 | 400 | 5.30 |
| Total: Effervescent Mix | | | 1500 | |
| CBD Oil (50%, 10mg) C16-60 | 15-25 | .15-.35 | 20 | 0.27 |
| Cayenne Extract (80% Alcohol) | 2-100 | .5-1.5 | 60 | 0.80 |
| Lemon Oil | .5-10 | .005-.1 | 5 | 0.07 |
| Quillaja | 5-25 | .1-.4 | 18.5 | 0.25 |
| MET5207 (Honey Flavor) | 50-500 | .5-5 | 100 | 1.33 |
| MET3636 (Green Tea Flavor) | 10-100 | .3-1 | 50 | 0.66 |
| MET0340 (Lemon Flavor) | 200-500 | 3-6 | 375 | 4.97 |
| MET0983 (Yellow Color) | 5-40 | .1-.5 | 15 | 0.20 |
| Fructose | 2300-2400 | 30-35 | 2320 | 30.74 |
| Sucrose | 2300-2400 | 30-35 | 2320 | 30.74 |
| Total: Flavor Mix | | | 5283.5 | |
| Total: | | | 7546.48 | 100.00 |

FIG. 4

Table 5: Dry Preparation for Calming - 5000

| Ingredient | Embodiment 1 Weight (mg) | Embodiment 2 Weight (%) | Embodiment 3 Weight (mg) | Embodiment 3 Weight (%) |
|---|---|---|---|---|
| Vitamin C (Ascorbic Acid) | 200-1000 | 7-9 | 600 | 7.98 |
| L-Theanine | 10-40 | .1-.5 | 24.75 | 0.33 |
| Folic Acid | .2-.6 | .005-.02 | 0.4 | 0.01 |
| Total: Vitamin Mix | | | 625.15 | |
| Sodium Bicarbonate | 250-1200 | 3-7 | 400 | 5.32 |
| Potassium Bicarbonate | 50-600 | .9-2 | 100 | 1.33 |
| Citric Acid | 300-1000 | 6-9 | 600 | 7.98 |
| Tartaric Acid | 200-1000 | 4-7 | 400 | 5.32 |
| Total: Effervescent Mix | | | 1500 | |
| CBD Oil (50%, 10mg) C16-60 | 15-25 | .15-.4 | 20 | 0.27 |
| Lavender Oil | 1-5 | .005-.09 | 2.15 | 0.03 |
| Quillaja | 7-25 | .05-.3 | 11.08 | 0.15 |
| Passionflower Extract | 5-20 | .05-.3 | 8 | 0.11 |
| MET0839 (Grapefruit Flavor) | 100-1000 | 4-10 | 550 | 7.32 |
| MET3805 (Beet Powder) | .5-5 | .005-.1 | 1 | 0.01 |
| Fructose | 2000-3000 | 30-35 | 2400 | 31.93 |
| Sucrose | 2000-3000 | 30-35 | 2400 | 31.93 |
| Total: Flavor Mix | | | 5392.23 | |
| Total: | | | 6892.23 | 100.0000 |

FIG. 5

Table 6: Dry Preparation for Soothing - 6000

| Ingredient | Embodiment 1 Weight (mg) | Embodiment 2 Weight (%) | Embodiment 3 Weight (mg) | Embodiment 3 Weight (%) |
|---|---|---|---|---|
| Vitamin C | 200-1000 | 5-7 | 500 | 6.66 |
| Glucosamine Sulfate | 1-200 | 1-3 | 100 | 1.33 |
| Vitamin D | .0001-.05 | .0001-.0007 | 0.02 | 0.0003 |
| Bromelain | 1-20 | .05-.2 | 10.08 | 0.13 |
| Total: Vitamin Mix | | | 610.1 | |
| Sodium Bicarbonate | 250-1200 | 4-6 | 400 | 5.33 |
| Potassium Bicarbonate | 50-600 | .9-2 | 100 | 1.33 |
| Citric Acid | 300-1000 | 6-10 | 600 | 8.00 |
| Tartaric Acid | 100-500 | 1-4 | 200 | 2.67 |
| Malic Acid | 100-500 | 2.5-4.5 | 270 | 3.60 |
| Total: Effervescent Mix | | | 1570 | |
| CBD Oil (50%, 10mg) C16-60 | 10-30 | .1-.35 | 20 | 0.27 |
| Turmeric Extract | 10-40 | .1-.3 | 15 | 0.20 |
| Cinnamon Oil | 5-15 | .05-.15 | 7 | 0.09 |
| Quillaja | 3-30 | .1-.5 | 21 | 0.28 |
| MET6376 (Cherry Flavor) | 250-750 | 6-10 | 550 | 7.33 |
| MET7987 (Red Color) | 10-50 | .2-.9 | 30 | 0.40 |
| Fructose | 2200-2500 | 30-35 | 2340 | 31.19 |
| Sucrose | 2200-2500 | 30-35 | 2340 | 31.19 |
| Total: Flavor Mix | | | 5323 | |
| Total: | | | 7503.1 | 100.0000 |

FIG. 6

CANNABINOID EMULSION PRODUCT AND PROCESS FOR MAKING THE SAME

CLAIM OF PRIORITY

This application is a continuation of U.S. application Ser. No. 15/462,495, filed Mar. 17, 2017 and entitled "Cannabinoid Emulsion Product and Process for Making the Same." U.S. application Ser. No. 15/462,495 claims priority to U.S. Provisional Application No. 62/310,079, entitled "Cannabinoid Emulsion Product and Process for Making the Same" and filed Mar. 18, 2016. All applications are incorporated herein by reference in their entirety.

BACKGROUND

Many dietary supplements, food ingredients, and foods are referred to as "nutraceuticals." An item is often referred to as a nutraceutical when it is believed to provide both a "nutritious" and "healthy" effect (i.e., the item has an effect similar to a pharmaceutical) to the person ingesting the item. Any food item which is purported to provide an extra health benefit in addition to the basic nutritional value of the food may be referred to as a nutraceutical.

Current products containing cannabinoids include edibles containing *cannabis* oil, powders and liquid emulsions. One problem with products on the market is that the cannabinoids are not soluble in water. Some products include an array of emulsifiers or surfactants such as glycerin, coconut oil, polysorbates, or other emulsifiers. These emulsified cannabinoids are most commonly used in liquid phase preparations for ease of use and maintaining the integrity of the emulsion. The powder preparations of cannabinoids are commonly prepared from purified and crystallized cannabinoids. These crystallized cannabinoids are not soluble in water. Additionally, powder preparations of cannabinoids create unstable emulsions when mixed with water.

SUMMARY

In one example, a dry consumable preparation is disclosed. The exemplary preparation has a bulking agent. The exemplary preparation also has at least one of a cannabinoid or a cannabinoid extract containing one or more cannabinoids. The at least one of the cannabinoid or the cannabinoid extract containing one or more cannabinoids is plated onto the bulking agent. The exemplary preparation also has an effervescence agent, the effervescence agent having sodium bicarbonate, potassium bicarbonate, and at least one acid, the at least one acid having at least one of citric acid, tartaric acid, or malic acid, the effervescence agent further having a ratio of the sodium bicarbonate to the potassium bicarbonate to the at least one acid. The ratio is configured to create a chemical pH buffering system at a targeted pH range when the dry consumable preparation is added to a targeted amount of water.

An exemplary method of making a dry consumable preparation is also disclosed. The exemplary method includes mixing at least one of a cannabinoid or a cannabinoid extract containing one or more cannabinoids with a bulking agent, whereby the at least one of the cannabinoid or the cannabinoid extract containing one or more cannabinoids is plated onto the bulking agent. The exemplary method also includes introducing an effervescence agent to the mixture, the effervescence agent having sodium bicarbonate, potassium bicarbonate, and at least one acid. The at least one acid has at least one of citric acid, tartaric acid, or malic acid. The effervescence agent further has a ratio of the sodium bicarbonate to the potassium bicarbonate to the at least one acid that is configured to create a chemical pH buffering system at a targeted pH range when the dry consumable preparation is added to a targeted amount of water.

BRIEF DESCRIPTION OF THE DRAWINGS

FIG. 1 is an ingredients list for a dry preparation for calming;

FIG. 2 is an ingredients list for a dry preparation for general wellness;

FIG. 3 is an ingredients list for a dry preparation for soothing;

FIG. 4 is an ingredients list for another dry preparation for general wellness;

FIG. 5 is an ingredients list for another dry preparation for calming;

FIG. 6 is an ingredients list for another dry preparation for soothing; and

DETAILED DESCRIPTION

Figure 7:
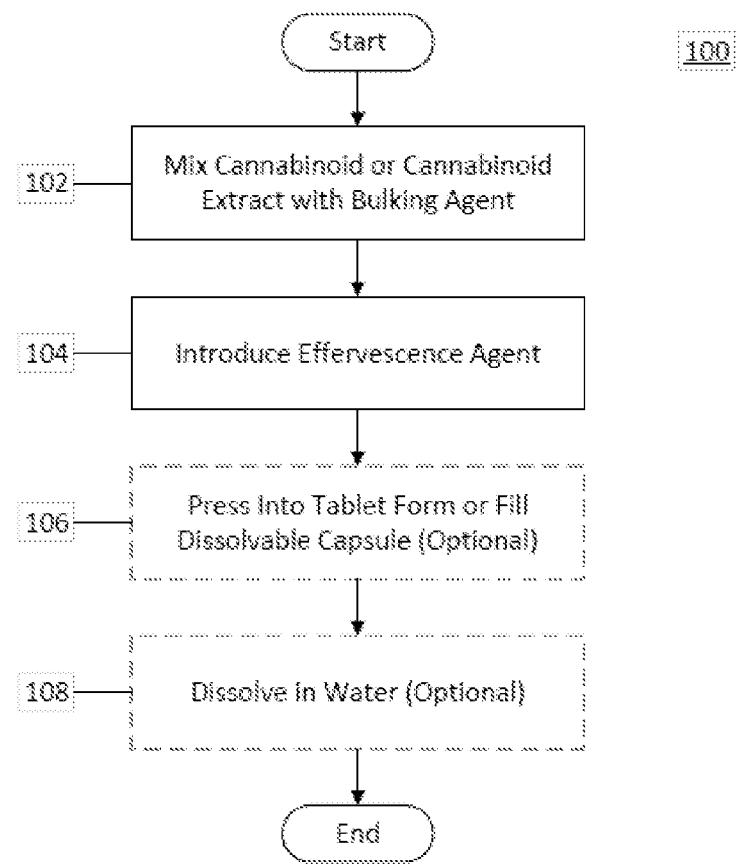
FIG. 7 is a flowchart of a method.

Cannabidiol (CBD) is one of at least eighty-five non-psychoactive chemical cannabinoid compounds found in a *cannabis* plant. CBD consumption has been shown to provide potential health benefits. For example, CBD may elicit antidepressant, anxiolytic, and neuroprotective effects on its users. Additional beneficial effects may also occur. Given the beneficial effects from CBD, it is contemplated to create one or more nutraceutical items that include CBD and other ingredients. One or more of the other ingredients may include other non-psychoactive cannabinoids such as, but not limited to, cannabigerol (CBG), cannabinol (CBN) and/or cannabichromene (CBC).

The insolubility of cannabinoids in water and the requirement for emulsifiers to maintain the cannabinoids in a water cannabinoid emulsion have prevented the creation of powder preparations of cannabinoids that are easily mixed and also create stable emulsions in water, thus presenting a long-felt and unmet need for a product that provides these benefits. The Applicant has created a dry preparation of cannabinoids and other nutrients. The formulation of the dry preparation may allow for easy mixing and create a stable emulsion in water. Some embodiments of the dry preparation are prepared so as to result in a liquid having an effervescence. Further, upon mixing with a liquid, some formulations of the Applicant's dry preparation may create a stable emulsion that resists the changes of pH after effervescence, and changes in other chemical characteristics of the solution that occur during effervescence.

The dry preparation may include a powder, a dissolvable capsule, and/or a tablet. The powder may be a loose powder. The capsule may include a gelatin coating. The capsule may encapsulate a powder. The tablet may be a compacted or pressed tablet. In some embodiments, the liquid may include water only. In some embodiments, the liquid may include tap water, purified water, mineral water, spring water, and/or any drinking water. In some embodiments, the liquid may include a liquid suitable for drinking, such as, but not limited to, water, milk, soda, and/or or fruit juice.

In some embodiments, a dry consumable preparation 1000, 2000, 3000, 4000, 5000, 6000 is provided. The preparation may have a bulking agent, at least one of a cannabinoid or a cannabinoid extract having one or more cannabinoids, and an effervescence agent. The cannabinoid or extract may be plated onto the bulking agent.

Those skilled in the art will recognize that plating is the process of turning a liquid or oil into a dry powder; specifically, the oil or liquid is to extended onto a dry edible carrier, and the resulting mixture behaves substantially as a powder would.

The effervescence agent may have sodium bicarbonate, potassium bicarbonate, and at least one acid. The acid may include citric acid, tartaric acid, and/or malic acid, and the effervescence agent may have a ratio of sodium bicarbonate to potassium bicarbonate to acid that is selected to create a chemical pH buffering system at a targeted pH range when the dry consumable preparation is added to a targeted amount of water. The bulking agent may include a sugar, such as fructose.

Three formulations are described herein generally, with ingredients for General Wellness 2000, 4000, Calming 1000, 5000, and Soothe 3000, 6000, with each having variations within. Each of these are formulated for the specific purpose of supporting general wellness and energy, supporting a calm and improved mood, and supporting joint health and combating inflammation respectively.

In some embodiments, the effervescence may enhance uptake of cannabinoids and buffering stomach acids, thereby protecting acid label cannabinoids.

Some examples described herein include CBD-based effervescent dry preparations and other products. Some dry preparations may provide various nutraceutical benefits to the user through the incorporation of one or more ingredients in addition to the CBD.

One such nutraceutical item may include an effervescent powder. The ingredients in an effervescent powder may include an acid and a base mixture. Upon mixing with water or another liquid, the acid and base mixture may interact, thereby producing carbon dioxide gas, which may accumulate and form bubbles. Those skilled in the art will recognize that the effervescent powder should be selected so as to provide an aqueous chemical environment that does not break the emulsion.

In some embodiments, an acid in the dry preparation may include citric acid. In some embodiments, the base in the dry preparation may include one or more bicarbonates such as, but not limited to, calcium bicarbonate, sodium bicarbonate, and/or potassium bicarbonate. In some embodiments, 1%, and up to 15%, or about 7%, of the effervescent powder may include the dried emulsion ingredients. Further ingredients may include vitamins, sugar and essential oil-based ingredients such as, but not limited to, terpenes. Terpenes may provide a nutraceutical synergy with CBD. For example, Beta-caryophyllene may include a terpene that may be included in the dry preparation. Beta-caryophyllene may be derived from a cinnamon essential oil. Additional ingredients adapted to stabilize the emulsion after mixing may also be included in the dry preparation. Additional ingredients may also be included in the dry preparation. For example, maltodextrin may be utilized as an ingredient.

As previously described, upon mixing the powder or tablet with a liquid such as, but not limited to, water, a bubbly and fizzy consumable mixture may be created. To realize the nutraceutical benefits associated with the dry preparation, a user may ingest the mixture immediately after mixing, during effervescence, or wait until after the effervescence has ceased, or wait about two to three minutes after the effervescence has ceased.

It may be preferable to consume during effervescence, which may impart advantages in palatability and delivery and absorption of the cannabinoid mixture and other nutrients within the formula.

In some embodiments, a consumable product having a liquid oil/water emulsion for use as a spray is provided. That is, a liquid emulsion having at least some of the features previously described as they relate to the dry preparation and emulsion may be provided, for use as a spray. In some embodiments, the spray may include an aqueous solution having a translucent or non-milky appearance. The spray may be used for general wellness, a calming effect, pain relief, and/or sleep benefits.

There may be a synergistic general wellness relationship between various terpenes and cannabinoids, and, in some embodiments, the cyclic terpene limonene may be used to provide one of these benefits, or any other benefit.

Some embodiments provide a water-based frozen consumable such, as, but not limited to, an ice pop. In some embodiments, the water-based frozen consumable may have an emulsion. In some embodiments, the water-based frozen consumable may have an effervescence upon melting in one's mouth. The water-based frozen consumable may have substantially all the ingredients described herein as they relate to an effervescent powder or tablet or emulsion. In addition to including one or more of the ingredients listed above, such as cannabidiol, which reduces muscle inflammation, other ingredients in the water-based frozen consumable may include flavored salts. The water-based frozen consumable may provide benefits to endurance athletes, cancer patients and/or other patients with a debilitating condition.

Those skilled in the art will recognize that the water-based frozen consumable may include a frozen emulsion where the emulsion is adapted to survive the liquid-to-solid phase transition. For example, oil may be added to an emulsifier at a high temperature, but without breaking the emulsion. An emulsifier may include a natural emulsifier such as, but not limited to, natural Quillaja tree extract, and/or any other emulsifier with a high HLB ratio. Quillaja may also provide a stabilizing effect on the resulting effervescent drink.

The HLB ratio is the ratio of Hydrophile-Lipophile Balance, which is an empirical expression for the relationship between the hydrophilic ("water-loving") and hydrophobic ("water-hating") groups of a surfactant. The higher the HLB ratio, the more water-soluble the surfactant or emulsifier.

In some embodiments, the water-based frozen consumable may include an emulsion created by using a high-shear mixer. Upon freezing, the oil in the mixture may be encapsulated by ice crystals, preventing oil from creating a layer on the ice pop packaging.

As previously described, some embodiments of the dry preparation may include a powder. The powder may include a fine, free-flowing effervescent, nutritional beverage powder infused with CBD. Such a powder may be combined with a person's desired liquid to create a beverage. One type of liquid may include water. Various ingredients may be needed to create such a powder.

For example, the powder may include one or more of: Sodium citrate, Magna Sweet, L-theanine, Passion flower flavor powder, Grapefruit essential oil, Lavender essential oil, Fructose, Sodium Bicarbonate, Calcium Carbonate, Potassium Carbonate, Citric Acid, Vitamin C, Coenzyme Q10, CBD oil, Quillaja, Cayenne extract, Lemon oil, Orange oil, Malic acid, Honey powder, Vitamin A, Vitamin D3, Vitamin B6, Vitamin B3, Vitamin B2, Vitamin B1, Vitamin B12, Zinc gluconate, Biotin, cherry flavor powder or other flavor powder, glucosamine sulfate, cinnamon essential oil, turmeric extract, and bromelain (600 GDU).

In some embodiments, the dry preparation 1000, 2000, 3000, 4000, 5000, 6000 may include more than 0.1% by weight of CBD oil. In some embodiments, the dry preparation may include more than 0.15% by weight of CBD oil. In some embodiments, the dry preparation may have up to 5% by weight CBD oil. In some embodiments, the dry preparation may have between 0.1% and 5% by weight CBD oil, or between 0.1% and 2% by weight CBD oil, or between 2% and 5% by weight CBD oil, or between about 0.05% and about 0.3% by weight CBD oil. In some embodiments, the preparation may have about 0.155% by weight CBD oil, or about 0.15% by weight CBD oil, or between about 0.05% and about 0.3% by weight CBD oil.

Those skilled in the art will recognize that the presence of Tetrahydrocannabinol (THC) above 0.3% in the final product is prohibited by federal law. Therefore, if THC is present in the CBD oil, a dilution factor must be sufficient to dilute the THC to a level below 0.3%. Should federal law change, those skilled in the art may recognize that particular ratios of THC to CBD may be particularly beneficial; however, embodiments described herein may be specifically designed to deliver CBD, and not any relevant amounts of THC.

The preparation 1000, 2000, 3000, 4000, 5000, 6000 may have a nutraceutical composition, the nutraceutical composition having an amount of Quillaja selected to impart a stabilizing and emulsifying effect when the preparation is mixed with a targeted amount of water. The preparation may also have one or more herbal extracts, and one or more nutrient vitamins or minerals, and may be formulated to form a stable, effervescent emulsion when mixed with a targeted amount of water.

Dry Preparation for Calming

Turning now to Table 1, examples of a dry preparation for calming 1000 are described. A dry preparation having the ingredients illustrated in Table 1 may produce a calming effect upon ingesting. Three embodiments of the dry preparation for calming are illustrated. Embodiment 3 is illustrated in both weight in grams and weight by ratio.

The dry preparation for calming 1000 may include between about 0.03% and about 0.05% by weight sodium citrate or about 0.0493% by weight sodium citrate. The dry preparation for calming may include between about 0.2% and about 0.5% by weight vitamin C, or about 0.3% by weight vitamin C. The dry preparation for calming 1000 may include between about 0.2% and about 0.5% by weight coenzyme Q10, or about 0.332% by weight coenzyme Q10. The dry preparation for calming 1000 may include between about 0.05% and about 0.2% by weight magna sweet, or about 0.113% by weight magna sweet. The dry preparation for calming 1000 may include between about 0.2% and about 0.5% by weight L Theanine, or about 0.331% by weight L Theanine. The dry preparation for calming 1000 may include between about 0.1% and about 0.3% by weight passionflower flavor powder or about 0.2% weight of passionflower flavor powder. The dry preparation for calming 1000 may include between about 0.05% and about 0.25% by weight CBD Oil (64.5%), or about 0.155% by weight CBD Oil (64.5% CBD). The dry preparation for calming 1000 may include between about 70% and about 80% by weight fructose, or about 76.036% by weight fructose. The dry preparation for calming 1000 may include between about 0.3% and about 0.5% by weight grapefruit oil, or about 0.429% by weight grapefruit oil. The dry preparation for calming 1000 may include between about 0.02% and about 0.04% by weight lavender oil, or about 0.029% by weight lavender oil. The dry preparation for calming 1000 may include between about 17% and about 19% by weight citric acid or about 17.699% by weight citric acid. The dry preparation for calming 1000 may include between about 0.7% and about 1.0% by weight sodium bicarbonate, or about 0.885% by weight sodium bicarbonate. The dry preparation for calming 1000 may include between about 0.8% and about 1.3% by weight calcium carbonate, or about 1.063% by weight calcium carbonate. The dry preparation for calming 1000 may have between about 2.0% and about 2.8% by weight potassium bicarbonate, or about 2.302% by weight potassium bicarbonate. The dry preparation for calming 1000 may have between about 0.05% and about 0.15% by weight Quillaja, or about 0.077% by weight Quillaja.

The dry preparation for calming 1000 may have a ratio of grapefruit oil to lavender oil of about 15:1. The dry preparation for calming 1000 may have a ratio of calcium carbonate to sodium bicarbonate of between about 1:1 and 2:1, or about 1.2:1. The dry preparation for calming 1000 may have a ratio of potassium bicarbonate to sodium bicarbonate of between about 2:1 and 3:1, or about 2.6:1. The dry preparation for calming 1000 may have a ratio of Quillaja to CBD oil of between about 1:1 and 1:4, or about 1:2.

Turning now to Table 2, examples of a dry preparation for general wellness 2000 are described. A dry preparation having the ingredients illustrated in Table 2 may provide wellness benefits upon ingesting on a short-term or long-term basis. Three embodiments of the dry preparation for wellness 2000 are illustrated. Embodiment 3 is illustrated in both weight in grams and weight by ratio.

The dry preparation for wellness 2000 may have between about 0.001% and about 0.003% by weight Vitamin A, or about 0.0027% by weight Vitamin A. The dry preparation for wellness 2000 may have between about 0.0001% and about 0.0003% by weight Vitamin D3, or about 0.0002% by weight Vitamin D3. The dry preparation for wellness 2000 may have between about 0.004% and about 0.008% by weight Vitamin B6, or about 0.006% by weight Vitamin B6. The dry preparation for wellness 2000 may have between about 0.03% and about 0.07% by weight Vitamin B3, or about 0.048% by weight Vitamin B3. The dry preparation for wellness 2000 may have between about 0.005% and about 0.03% by weight Vitamin B2, or about 0.0173% Vitamin B2. The dry preparation for wellness 2000 may have between about 0.005% and about 0.03% by weight Vitamin B1, or about 0.0173% by weight Vitamin B1. The dry preparation for wellness 2000 may have between about 0.0004% and about 0.0008% by weight Vitamin B12, or about 0.0006% by weight Vitamin B12. The dry preparation for wellness may have between about 0.1% and about 0.5% by weight Vitamin C, or about 0.30% by weight Vitamin C. The dry preparation for wellness 2000 may have between about 0.01% and about 0.04% by weight zinc gluconate, or about 0.024% by weight zinc gluconate. The dry preparation for wellness 2000 may have between about 0.005% and about 0.003% by weight Biotin, or about 0.0013% by weight Biotin. The dry preparation for wellness 2000 may have between about 0.3% and about 0.7% by weight malic acid, or about 0.57% by weight malic acid. The dry preparation for wellness 2000 may have between about 0.05% and about 0.2% by weight sodium citrate, or about 0.11% by weight sodium citrate. The dry preparation may have between about 0.04% and about 0.09% by weight honey powder, or about 0.07% by weight honey powder. The dry preparation for wellness 2000 may have between about 0.05% and about 0.3% by weight magna sweet, or about 0.14% by weight magna sweet. The dry preparation for wellness 2000 may have between about 0.1% and about 0.3% by weight green tea flavor powder or other flavor, or about 0.20% by weight green tea flavor powder or other flavor. The dry preparation for wellness 2000 may have between about 0.05% and about 0.5% by weight CBD oil, or about 0.15% by weight CBD oil. The dry preparation for wellness 2000 may have between about 0.005% and about 0.2% by weight Quillaja, or about 0.08% by weight Quillaja. The dry preparation for wellness 2000 may have between about 0.2% and about 0.6% by weight lemon oil, or about 0.47% by weight lemon oil. The dry preparation for wellness 2000 may have between about 0.2% and about 0.5% by weight orange oil, or about 0.36% by weight orange oil. The dry preparation for wellness 2000 may have between about 0.05% and about 0.3% by weight cayenne extract, or about 0.16% by weight cayenne extract. The dry preparation for wellness 2000 may have between about 68% and about 79% by weight fructose, or about 73.62% by weight fructose. The dry preparation for wellness 2000 may have between about 1% and about 2% by weight sodium bicarbonate, or about 1.57% by weight sodium bicarbonate. The dry preparation for wellness 2000 may have between about 0.5% and about 1.5% by weight calcium carbonate, or about 1.08% by weight calcium carbonate. The dry preparation for wellness 2000 may have between about 2.5% and about 3.5% by weight potassium bicarbonate, or about 3.13% by weight potassium bicarbonate. The dry preparation for wellness 2000 may have between about 16.5% and about 18.5% by weight citric acid, or about 17.86% by weight citric acid.

Turning now to Table 3, examples of a dry preparation for soothing 3000 are described. A dry preparation having the ingredients illustrated in Table 3 may provide benefits upon ingesting on a short-term or long-term basis. The benefits may include but are not limited to reduction in inflammation, strong cartilage and healthy joints, and an increase in antioxidant activity, preventing cellular damage and stress. Three embodiments of the dry preparation for soothing 3000 are illustrated. Embodiment 3 is illustrated in both weight in grams and weight by ratio.

The dry preparation for soothing 3000 may have between about 0.5% and about 1.5% by weight sodium citrate, or about 0.12% by weight sodium citrate. The dry preparation for soothing 3000 may have between about 0.2% and about 0.4% by weight Vitamin C, or about 0.3% by weight Vitamin C. The dry preparation for soothing 3000 may have between about 0.1% and about 0.3% by weight cherry flavor or other flavor powder, or about 0.2% by weight cherry flavor or other flavor powder. The dry preparation for soothing 3000 may have between about 0.5% and about 0.2% by weight CBD oil, or about 0.15% by weight CBD oil. The dry preparation for soothing 3000 may have between about 0.9% and about 2.0% glucosamine sulfate, or about 1.33% by weight glucosamine sulfate. The dry preparation for soothing 3000 may have between about 0.0001% and about 0.0005% Vitamin D, or about 0.0003% by weight Vitamin D. The dry preparation for soothing 3000 may have between about 0.05% and about 0.2% by weight bromelain, or about 0.13% by weight bromelain. The dry preparation for soothing 3000 may have between about 0.05% and about 0.09% by weight Quillaja, or about 0.08% by weight Quillaja. The dry preparation for soothing 3000 may have between about 0.07% and about 0.15% by weight magna sweet, or about 0.09% by weight magna sweet. The dry preparation for soothing 3000 may have between about 75% and about 80% by weight fructose G, or about 78.37% by weight fructose G. The dry preparation for soothing 3000 may have between about 0.1% and about 0.4% by weight cinnamon oil, or about 0.28% by weight cinnamon oil. The dry preparation for soothing 3000 may have between about 0.5% and about 1.2% by weight turmeric extract, or about 0.77% by weight turmeric extract. The dry preparation for soothing 3000 may have between about 13% and about 16% by weight citric acid, or about 14.27% by weight citric acid. The dry preparation for soothing 3000 may have between about 0.8% and about 1.5% by weight sodium bicarbonate, or about 1.19% by weight sodium bicarbonate. The dry preparation for soothing 3000 may have between about 0.5% and about 1.3% by weight calcium carbonate, or about 0.86 calcium carbonate. The dry preparation for soothing 3000 may have between about 1.4% and about 2.5% by weight potassium bicarbonate, or about 1.85% by weight potassium bicarbonate.

Turning now to Table 4, examples of another dry preparation for wellness 4000 are described. A dry preparation having the ingredients illustrated in Table 4 may provide benefits upon ingesting on a short-term or long-term basis. Three embodiments of the dry preparation for wellness 4000 are illustrated. Embodiment 3 is illustrated in both weight in milligrams and weight by ratio.

The dry preparation for wellness 4000 may have between about 0.0005% and about 0.002% by weight biotin or Vitamin B7, or about 0.001% by weight biotin or Vitamin B7. The dry preparation for wellness 4000 may have between about 0.002% and about 0.004% by weight Vitamin A or Palmitate, or about 0.003% by weight Vitamin A or Palmitate. The dry preparation for wellness 4000 may have between about 0.015% and about 0.03% by weight Vitamin B1 or Thiamine HCL, or about 0.02% by weight Vitamin B1 or Thiamine HCL. The dry preparation for wellness 4000 may have between about 0.015% and about 0.03% by weight Vitamin B2 or Riboflavin, or about 0.03% by weight Vitamin B2 or Riboflavin. The dry preparation for wellness 4000 may have between about 0.04% and about 0.06% by weight Vitamin B3 or Niacin USP or about 0.05% by weight Vitamin B3 or Niacin USP. The dry preparation for wellness 4000 may have between about 0.05% and about 0.07% by weight Vitamin B6 or Pyridoxine HCL, or about 0.06% by weight Vitamin B6 or Pyridoxine HCL. The dry preparation for wellness 4000 may have between about 0.0005% and about 0.003% by weight Vitamin B12 or Cyanocobalamin, or about 0.001% Vitamin B12 or Cyanocobalamin. The dry preparation for wellness 4000 may have between about 2% and about 20% by weight Vitamin C or ascorbic acid, or about 9.94% by weight Vitamin C or ascorbic acid. The dry preparation for wellness 4000 may have between about 0.00005% and about 0.0002% by weight Vitamin D3 or cholecalciferol, or about 0.0001% by weight Vitamin D3 or cholecalciferol. The dry preparation for wellness 4000 may have between about 0.015% and about 0.03% by weight zinc gluconate, or about 0.02% by weight zinc gluconate. The dry preparation for wellness 4000 may have between about 2% and about 15% by weight sodium bicarbonate, or about 5.3% by weight sodium bicarbonate. The dry preparation for wellness 4000 may have between about 1% and about 8% by weight potassium bicarbonate, or about 1.33% by weight potassium bicarbonate. The dry preparation for wellness 4000 may have between about 5% and 10% by weight citric acid, or about 7.95% by weight citric acid. The dry preparation for wellness 4000 may have between about 4% and about 10% by weight tartaric acid, or about 5.3% by weight tartaric acid. The dry preparation for wellness 4000 may have between about 0.15% and about 0.35% by weight CBD oil (50%, 10 mg) C16-60, or about 0.25% by weight CBD Oil. The dry preparation for wellness 4000 may have between about 0.5% and about 1.5% by weight cayenne extract (80% alcohol), or about 0.8% by weight cayenne extract. The dry preparation for wellness 4000 may have between about 0.005% and about 0.1% by weight lemon oil, or about 0.07% by weight lemon oil. The dry preparation for wellness 4000 may have between about 0.1% and about 0.4% Quillaja, or about 0.25% by weight Quillaja. The dry preparation for wellness 4000 may have between about 0.5% and about 5% by weight honey flavor or other flavor, or about 1.33% by weight honey flavor or other flavor. The dry preparation for wellness 4000 may have between about 0.3% and about 1% by weight green tea flavor, or about 0.66% by weight green tea flavor.

The dry preparation for wellness 4000 may have between about 3% and about 6% by weight lemon flavor or other flavor, or about 4.97% by weight lemon flavor or other flavor. The dry preparation for wellness 4000 may have between about 0.1% and about 0.5% by weight yellow color, or about 0.2% by weight yellow color. The dry preparation for wellness may have between about 30% and about 35% by weight fructose, or about 30.74% by weight fructose. The dry preparation for wellness may have between about 30% and about 35% by weight sucrose, or about 30.74% by weight sucrose.

The dry preparation for wellness 4000 may have a ratio of sodium bicarbonate to potassium bicarbonate of between about 2:1 and about 5:1. The dry preparation for wellness 4000 may have a ratio of sodium bicarbonate to potassium bicarbonate of about 4:1. The dry preparation for wellness 4000 may have a ratio of Quillaja to CBD oil of between about 1:1 and about 1:4. The dry preparation for wellness 4000 may have a ratio of Quillaja to CBD oil of about 1:2. The dry preparation for wellness 4000 may have a ratio of fructose to sucrose of between about 1:0.75 and about 1:1. The dry preparation for wellness 4000 may have a ratio of fructose to sucrose of about 1:1.

Turning now to Table 5, examples of another dry preparation for calming 5000 are described. A dry preparation having the ingredients illustrated in Table 5 may provide benefits upon ingesting on a short-term or long-term basis. Three embodiments of the dry preparation for calming 5000 are illustrated. Embodiment 3 is illustrated in both weight in milligrams and weight by ratio.

The dry preparation for calming 5000 may have between about 7% and about 9% by weight Vitamin C or ascorbic acid, or about 7.98% by weight Vitamin C or ascorbic acid. The dry preparation for calming 5000 may have between about 0.1% and about 0.5% by weight L-Theanine, or about 0.33% by weight L-Theanine. The dry preparation for calming 5000 may have between about 0.005% and about 0.02% by weight folic acid, or about 0.01% by weight folic acid. The dry preparation for calming 5000 may have between about 3% and about 7% by weight sodium bicarbonate, or about 5.32% by weight sodium bicarbonate. The dry preparation for calming 5000 may have between about 0.9% and about 2% by weight potassium bicarbonate, or about 1.33% by weight potassium bicarbonate. The dry preparation for calming 5000 may have between about 6% and about 9% citric acid, or about 7.98% by weight citric acid. The dry preparation for calming 5000 may have between about 4% and about 7% by weight tartaric acid, or about 5.32% by weight tartaric acid. The dry preparation for calming 5000 may have between about 0.15% and about 0.4% by weight CBD oil (50%, 10 mg) C16-60, or about 0.27% by weight CBD oil. The dry preparation for calming 5000 may have between about 0.005% and about 0.09% by weight lavender oil, or about 0.03% by weight lavender oil. The dry preparation for calming 5000 may have between about 0.05% and about 0.3% by weight Quillaja, or about 0.15% by weight Quillaja. The dry preparation for calming 5000 may have between about 0.05% and about 0.3% passionflower extract, or about 0.11% by weight passionflower extract. The dry preparation for calming 5000 may have between about 4% and about 10% by weight grapefruit flavor or other flavor, or about 7.32% by weight grapefruit flavor or other flavor. The dry preparation for calming 5000 may have between about 0.005% and about 0.1% by weight beet powder, or about 0.01% by weight beet powder. The dry preparation for calming 5000 may have between about 30% and about 35% by weight fructose, or about 31.93% by weight fructose. The dry preparation for calming 5000 may have between about 30% and about 35% by weight sucrose, or about 31.93% by weight sucrose.

The dry preparation for calming 5000 may have a ratio of sodium bicarbonate to potassium bicarbonate of between about 2:1 and about 5:1. The dry preparation for calming 5000 may have a ratio of sodium bicarbonate to potassium bicarbonate of about 4:1. The dry preparation for calming 5000 may have a ratio of Quillaja to CBD oil of between about 1:1 and about 1:4. The dry preparation for calming 5000 may have a ratio of Quillaja to CBD oil of about 1:2. The dry preparation for calming 5000 may have a ratio of fructose to sucrose of between about 1:0.75 and about 1:1.25. The dry preparation for calming 5000 may have a ratio of fructose to sucrose of about 1:1.

Turning now to Table 6, examples of another dry preparation for soothing 6000 are described. A dry preparation having the ingredients illustrated in Table 6 may provide benefits upon ingesting on a short-term or long-term basis. Three embodiments of the dry preparation for soothing 6000 are illustrated. Embodiment 3 is illustrated in both weight in milligrams and weight by ratio.

The dry preparation for soothing 6000 may have between about 5% and about 7% by weight Vitamin C, or about 6.66% by weight Vitamin C. The dry preparation for soothing 6000 may have between about 1% and about 3% by weight glucosamine sulfate, or about 1.33% by weight glucosamine sulfate. The dry preparation for soothing 6000 may have between about 0.0001% and about 0.0007% by weight Vitamin D, or about 0.0003% by weight Vitamin D. The dry preparation for soothing 6000 may have between about 0.05% and about 0.2% by weight bromelain, or about 0.13% by weight bromelain. The dry preparation for soothing 6000 may have between about 4% and about 6% by weight sodium bicarbonate, or about 5.33% by weight sodium bicarbonate. The dry preparation for soothing 6000 may have between about 0.9% and about 2% by weight potassium bicarbonate, or about 1.33% by weight potassium bicarbonate. The dry preparation for soothing 6000 may have between about 6% and about 10% by weight citric acid, or about 8% by weight citric acid. The dry preparation for soothing 6000 may have between about 1% and about 4% by weight tartaric acid, or about 2.67% by weight tartaric acid. The dry preparation for soothing 6000 may have between about 2.5% and about 4.5% by weight malic acid, or about 3.6% by weight malic acid. The dry preparation for soothing 6000 may have between about 0.1% and about 0.35% by weight CBD oil (50%, 10 mg) C16-60, or about 0.27% by weight CBD oil. The dry preparation for soothing 6000 may have between about 0.1% and about 0.3% by weight turmeric extract, or about 0.2% by weight turmeric extract. The dry preparation for soothing 6000 may have between about 0.05% and about 0.15% by weight cinnamon oil, or about 0.09% by weight cinnamon oil. The dry preparation for soothing 6000 may have between about 0.1% and about 0.5% by weight Quillaja, or about 0.28% by weight Quillaja. The dry preparation for soothing 6000 may have between about 6% and about 10% by weight cherry flavor or other flavor, or about 7.33% by weight cherry flavor or other flavor. The dry preparation for soothing 6000 may have between about 0.2% and about 0.9% by weight red color or other color, or about 0.4% by weight red color or other color. The dry preparation for soothing 6000 may have between about 30% and about 35% by weight fructose, or about 31.19% by weight fructose. The dry preparation for soothing 6000 may have between about 30% and about 35% by weight sucrose, or about 31.19% by weight sucrose.

The dry preparation for soothing 6000 may have a ratio of sodium bicarbonate to potassium bicarbonate of between about 2:1 and about 5:1. The dry preparation for soothing 6000 may have a ratio of sodium bicarbonate to potassium bicarbonate of about 4:1. The dry preparation for soothing 6000 may have a ratio of Quillaja to CBD oil of between about 1:1 and about 1:4. The dry preparation for soothing 6000 may have a ratio of Quillaja to CBD oil of about 1:2. The dry preparation for soothing 6000 may have a ratio of fructose to sucrose of between about 1:0.75 and about 1:1.25. The dry preparation for soothing 6000 may have a ratio of fructose to sucrose of about 1:1.

Turning now to FIG. 1, a method 100 of making a dry consumable preparation is now described. The method 100 may be used to make a dry preparation, such as the dry preparations for calming 1000, 5000 illustrated in Tables 1 or 5, the dry preparations for wellness 2000, 4000 illustrated in Tables 2 or 4, or the dry preparations for soothing 3000, 6000 illustrated in Tables 3 or 6. The method 100 may be implemented to produce about 7500 g of dry preparation 1000, 2000, 3000, 4000, 5000, 6000. Those skilled in the art will recognize that although the illustrated ingredients listings are scaled to about 7500 g of dry preparation, any scaling is suitable based off the weight in grams or milligrams, and such scaling is within the scope of this disclosure.

The method 100 of making a dry consumable preparation includes mixing 102 at least one of a cannabinoid or a cannabinoid extract containing one or more cannabinoids with a bulking agent. Mixing 102 may include mixing whereby the at least one of the cannabinoid or the cannabinoid extract containing one or more cannabinoids is plated onto the bulking agent. For example, those skilled in the art will recognize that the cannabinoid or cannabinoid extract containing one or more cannabinoids may be an oil. Mixing with the bulking agent and causing the oil to plate onto the bulking agent will cause the resulting mixture to behave like a dry product, because the oil is substantially encased. Mixing 102 may also include mixing any other oils included in the preparation and causing the oils to plate onto the bulking agent.

The method 100 also includes introducing 104 an effervescence agent to the mixture formed by the mixing 102. The effervescence agent may include sodium bicarbonate, potassium bicarbonate, and at least one acid. The at least one acid may include citric acid, tartaric acid, and/or malic acid. The effervescence agent may have a particular ratio of sodium bicarbonate to potassium bicarbonate acid. The ratio may be configured or selected to create a chemical pH buffering system at a targeted pH range when the dry consumable preparation is added to a targeted amount of water. Of note, a higher pH is associated with a less stable emulsion, with a pH of less than 2 being particularly unstable. At the same time, a lower pH results in less $CO_2$ being released during effervescence, while a higher pH generates more $CO_2$. The Applicants have determined that a pH of between 2 and 6, or between 4 and 5, may be suited to maximize the balance between nutrient uptake (nutrient uptake may be associated with effervescence) and a stable emulsion, as well as taste.

The method 100 may include pressing the mixture formed by the mixing 102 and the introducing 104 into a tablet form or filling the mixture into a dissolvable capsule 106.

The method 100 may include dissolving 108 the mixture formed by the mixing and the introducing 104 in a targeted amount of water.

The method 100 may produce an effervescence when combined with water. The powder formed by mixing 102 and introducing 104 may be configured to produce a stable emulsion in water which is maintained throughout the effervescence process. In some embodiments, the emulsion is maintained for several hours before degrading.

The method 100 may include providing enough CBD oil to deliver between about 5.0 g and 10.0 g, or about 7.5 g CBD across 1000 servings. Providing may include providing the CBD oil in a stainless steel mixing container or any mixing container suitable for mixing the dry preparation. In some embodiments, a CBD oil concentration mix may be used. In some embodiments, a CBD oil concentration mix having about 64.5% CBD may be used. When using a 64.5% CBD concentration, 11.6 g of CBD oil should be used to provide 7.5 g of CBD across 1000 servings (7.5 g/0.645=11.6 g). Those skilled in the art will recognize that the remainder of the CBD oil concentration mixture may include fatty acids, flavonoids (flavor), terpenoids (aroma), carotenoids (color), waxes, chlorophyll, and other plant lipids. It is contemplated that the total concentration of CBD in each serving is less than 1%, or less than 0.5%, or less than 0.1%.

The method 100 may also include providing a bulking agent. The bulking agent may include or be a sweetener. The bulking agent may include fructose. Providing the bulking agent may include determining the amount of fructose or bulking agent to use. For example, the quantity of fructose may be dependent on the quantity of CBD oil used. For any given amount of CBD oil, the amount of fructose may be increased or decreased to reach a 7,500 g final powder weight. Fructose may be added as a bulking agent to adjust weight and to give the powder a sweet flavor, acting as a masking agent to the bitter CBD flavor.

The method 100 may include providing a first group of ingredients. This first group of ingredients may include any essential oil desired to be included in the product, along with a botanical extract and/or quillaja. For example, to produce the dry preparation for calming 1000 illustrated in Table 1, providing may include combining grapefruit and lavender essential oils along with Quillaja in a first mixing container and introducing this mix to the container having the bulking agent and CBD oil. In some embodiments, 25 g to 50 g, or about 32.1 g of grapefruit essential oil, an amount of lavender essential oil equal to the ratio of 15:1 grapefruit oil:lavender oil, and an amount of Quillaja equal to a ratio of about 1:1 to 1:4, or a ratio of about 1:2 Quillaja:oil are mixed together and then introduced to the container having the bulking agent and CBD oil.

To produce the dry preparation for wellness illustrated in Table 2, 10 g to 50 g, or about 35.0 g lemon essential oil, and an amount of orange essential oil equal to the ratio of about 0.5:1 to 1.5:1, or about 0.75:1 orange essential oil:lemon essential oil may be combined in a first mixing container and then introduced to the mix having the bulking agent and CBD oil.

To produce the dry preparation for soothing 3000 for soothing, 5 g to 50 g, or about 21.0 g cinnamon essential oil, 10 g to 100 g, or about 57.4 g turmeric extract, and an amount of quillaja equal to a ratio of about 1:1 to 1:4, or a ratio of about 1:2 quillaja:oil may be combined.

Providing the first group of ingredients may include providing ingredients that provide the user with nutraceutical properties associated with the ingredients.

Providing may include mixing the first group of ingredients, the bulking agent, and the CBD oil.

The method 100 may include allowing the mixture of CBD oil, bulking agent, and first group of ingredients to stand for a period of time. The period of time may be at least 2 minutes. The period of time may be between about 2 minutes and about 5 minutes. The period of time may be less than 10 minutes. The period of time may be a period of time suitable for allowing the mixture to homogenize. The ingredients should then be mixed with the CBD oil well enough for the CBD oil to homogenize.

The method may include introducing the previously mixed ingredients to fructose. To prepare the dry preparation for calming illustrated in Table 1 or Table, the previously mixed ingredients may be introduced to between about 5,693 g and about 5,710 g, or about 5,703 g of fructose. To prepare the dry preparation for wellness illustrated in Table 2, the previously mixed ingredients may be introduced to between about 5,495 g and about 5,523 g, or about 5,517 g of fructose. To prepare the dry preparation for soothing 3000, the previously mixed ingredients may be introduced to between about 5,850 g and about 5,881 g, or about 5,870 g of fructose. Introducing may include introducing while mixing the fructose. Introducing may include introducing in a manner that prevents clumping. For example, the fructose may be in a mixing container set on a low setting, and the previously mixed ingredients may be slowly introduced over a period of several minutes.

Introducing may include determining whether clumps are forming. If so, introducing may include pausing the introducing to scrape the container and break down clumps. This may occur about every 60 seconds. The mixing device or container may be powered off to allow for a user to scrape an interior of the mixing bowl to break up clumps that have formed. Introducing may include introducing into a vertical cutter mixer (VCM).

The VCM may be used at a low mixing speed to thoroughly combine the ingredients, and it may be necessary to continue to power off or pause the device in order to scrape the sides or other portions of the mixing device to break up clumps every 30-60 seconds. Mixing and scraping occurs until the powder is homogenous, at which point the remainder of the dry ingredients may be added to the mixture.

The method 100 may include introducing the remaining ingredients. Introducing the remaining ingredients may include mixing thoroughly. To provide dry preparation for calming illustrated in Table 1, the remaining ingredients may include about 3 g to 10 g or about 3.7 g of sodium citrate, about 20 g to 100 g or about 22.5 g of Vitamin C, about 20 g to 50 g or about 24.9 g of Coenzyme Q10, about 5 g to 10 g or about 8.5 g of Magna Sweet, about 20 g to 50 g or about 24.7 g of L-theanine, about 10 g to 20 g or about 15.0 g of passionflower flavor powder, about 1,300 g to 1,400 g about 1,327 g citric acid, about 60 g to 120 g or about 66.4 g sodium bicarbonate, an amount of calcium carbonate equal to the ratio of 1:1 to 2:1, or about 1.2:1 calcium carbonate: sodium bicarbonate, and an amount of potassium bicarbonate equal to the ratio of 2:1 to 3:1, or about 2.6:1 potassium bicarbonate:sodium bicarbonate, to the container or VCM bowl.

To produce the dry preparation for wellness illustrated in Table 2, the remaining ingredients may include about 1 g to 50 g or about 11.9 g of cayenne extract, which may be added and mixed prior to adding the reminder of the dry ingredients including about 0.1 g to 0.3 g or about 0.2 g Vitamin A, about 0.0075 g to 0.03 g or about 0.015 g Vitamin D3, about 4 g to 5 g or about 4.5 g Vitamin B6, about 3 g to 5 g or about 3.6 g Vitamin B3, about 1 g to 2 g or about 1.3 g Vitamin B2, about 1 g to 2 g or about 1.3 g Vitamin B1, about 0.04 g to 0.05 g or about 0.046 g Vitamin B12, about 20 g to 100 g or about 22.5 g Vitamin C, about 1 g to 2 g or about 1.8 g zinc gluconate, about 0.05 g to 0.2 g or about 0.1 g Biotin, about 60 g to 120 g or about 117.0 g sodium bicarbonate, an amount of calcium carbonate equal to the ratio of about 0.5:1 to 1:1 or about 0.7:1 calcium carbonate:sodium bicarbonate, an amount of potassium bicarbonate equal to the ratio of about 1:5 to 3:1 or about 2:1 potassium bicarbonate:sodium bicarbonate, and 1,000 g to 2,000 g or about 1,338.1 g citric acid.

To prepare the Table 3 preparation, the remaining ingredients may include about 3 g to 10 g or about 8.8 g sodium citrate, about 20 g to 100 g or about 22.5 g Vitamin C, about 5 g to 25 g or about 15.0 g Cherry flavor powder, about 10 g to 200 g or about 99.9 g glucosamine sulfate, about 0.0075 g to 0.03 g or about 0.02 g Vitamin D, about 1 g to 20 g or about 10.1 g bromelain, about 5 g to 20 g or about 6.9 g Magna Sweet, about 1,000 g to 2,000 g citric acid or about 1,069.1 g citric acid, about 60 g to 120 g or about 89.1 g sodium bicarbonate, an amount of calcium carbonate equal to the ratio of about 0.5:1 to 1:1 or about 0.7:1 calcium carbonate:sodium bicarbonate, and an amount of potassium bicarbonate equal to the ratio of about 1:1 to 2:1 or about 1.5:1 potassium bicarbonate:sodium bicarbonate.

Introducing any ingredients may include introducing enough to provide a therapeutically effective amount of the ingredients, such as to provide the user with the nutraceutical properties and/or flavoring associated with each ingredient.

For example, a high level of Vitamin D may reduce chronic pain and inflammation from fibromyalgia. Furthermore, Magna Sweet includes a super sugar ingredient, made up of glycyrrhizic acid which is derived from licorice root. The Magna Sweet may also reduce the bitterness of the CBD, providing a prolonged sweetness on the tongue. Introducing may include mixing thoroughly, in a manner similar to that described with reference to introducing. For example, the mixing device may be powered on to a low mixing setting and allowed to thoroughly combine the ingredients, with the user or device periodically scraping the sides of the mixing device and breaking up and clumps as necessary until the powder is homogenous.

As previously described, the dry preparation 1000, 2000, 3000, 4000, 5000, 6000 may include a powder mixture having one or more cannabinoids, cannabinoid extract containing one or more cannabinoids, sucrose, fructose, Quillaja, one or more herbal extracts, one or more nutrient vitamins and minerals, and an effervescence mixture, wherein the powder composition forms a stable, effervescent emulsion when mixed with water.

The one or more herbal extracts may include Cayenne extract, Lemon oil, Turmeric extract, cinnamon oil, bromelain, lavender oil, tart cherry, and passion flower extract.

The one or more herbal extracts may be an essential oil.

The one or more vitamins and minerals may include L-theanine, Vitamin C, Folic Acid, Vitamin D, Glucosamine Sulfate, Biotin, Vitamins A, B1, B2, B3, B6, B12, and zinc gluconate.

In some embodiments, the effervescence mixture includes sodium bicarbonate, potassium bicarbonate, Citric acid, tartaric (taste effervescent quality/length of effervescence) acid, and Malic acid. Further, the ratio of sodium bicarbonate to potassium bicarbonate to acid (e.g., Citric acid, tartaric acid, Malic acid, or any other suitable acid) when added to water creates a chemical pH buffering system at a target pH range. The targeted pH range may be between about 2 and about 6. The targeted pH range may be between about 3 and 4. This chemical pH buffer system may resist changes to the target pH band of the effervescent powder/water solution. For example, the addition of excess acid, such as from mixing the effervescent powder with a fruit juice for example, would result in a small change in the pH of the effervescent powder/juice solution from the target pH band. The chemical pH buffering system provides the advantage of maintaining the pH of the effervescent powder water solution within a narrow target pH band to promote stability of the emulsion.

In addition to establishing the chemical pH buffering system, the effervescence created by the effervescent powder may impart advantages in palatability and delivery and absorption of the cannabinoid mixture and other nutrients within the formula. The presence of the carbon dioxide bubbles has been shown to enhance absorption of vitamins and minerals in the digestive tract. Further, effervescence has been shown to reduce stomach upset. Additionally, effervescence may be used to mask the bitter taste of some of the bitter flavonoids and biomolecules that may be present in cannabinoid oils and isolates, such as piperidine, for example.

The cannabinoid extract may be a cannabinoid oil or cannabinoid isolate. Further, the cannabinoid extract may be in liquid, crystalline, or liquid crystalline form.

As illustrated in Table 4, a general wellness formula 4000 may include a complex of B Vitamins, Vitamin C. Vitamin D3, zinc gluconate, Vitamin A, Cayenne Pepper extract, Lemon Oil, and Cannabidiol to promote immune system health (Vitamin C), improve energy (B Vitamin complex, zinc, Cayenne Pepper extract, and Lemon Oil), reduce inflammation (Cannabidiol and Cayenne Pepper extract), support bone health (Vitamin D3) and support vision and reduce oxidative stress (Vitamin A).

As illustrated in Table 5, a calm formula may include Vitamin C, L-theanine, Folic Acid, lavender oil, passionflower extract, and cannabidiol to promote a calm mood (L-theanine, Cannabidiol, lavender oil, and passionflower extract) and promote more efficient cellular energy metabolism which has been shown to aid in overcoming depression.

As illustrated in Table 6, a soothe formula may include Vitamin C, Vitamin D, Bromelain, Glucosamine sulfate, and Cannabidiol to reduce inflammation in the body (Cannabidiol and Bromelain) and support joint health (Vitamin D and Glucosamine Sulfate). red color provides a source of cyanidin which is a free radical scavenger and has antioxidant properties.

The effervescence is achieved through the reaction of sodium bicarbonate, potassium bicarbonate, citric acid and tartaric acid in water. This reaction releases carbon dioxide. It will be appreciated that coated versions of these ingredients or other suitable acids and bases may be used to prolong effervescence. Further, the tartaric acid and malic acid are used to improve flavor and reduce clumping due to these acids being less hygroscopic than citric acid.

In some embodiments, a ratio of sucrose to fructose of about 1:1 by weight is provided in the dry preparation 1000, 2000, 3000, 4000, 5000, 6000. This ratio creates an adequately sweet but not overly sweet emulsion consumption mediates the hygroscopicity of the fructose which prolongs the shelf-life of the product.

Those skilled in the art can readily recognize that numerous variations and substitutions may be made in the invention, its use and its configuration to achieve substantially the same results as achieved by the embodiments described herein. Accordingly, there is no intention to limit the invention to the disclosed exemplary forms. Many variations, modifications and alternative constructions fall within the scope and spirit of the disclosed invention as expressed in the claims.

What is claimed is:

1. A dry consumable preparation comprising:
   a bulking agent;
   at least one of a cannabinoid or a cannabinoid extract containing one or more cannabinoids, the at least one of the cannabinoid or the cannabinoid extract containing one or more cannabinoids plated onto the bulking agent;
   an effervescence agent, the effervescence agent having sodium bicarbonate, potassium bicarbonate, and at least one acid, the at least one acid having at least one of citric acid, tartaric acid, or malic acid, wherein a weight ratio of the effervescence agent to the at least one acid ranges from 0.5:0.5 to 4.0:30.0; and wherein the dry consumable preparation provides for at least two hours a water emulsion having a pH between 2 and 6.

2. The dry consumable preparation of claim 1, wherein the bulking agent comprises sucrose and fructose; and
   a ratio of the sucrose to the fructose by weight is between 1:0.75 and 1:1.25.

3. The dry consumable preparation of claim 2, wherein the preparation comprises at least 30% by weight of sucrose; and
   the preparation comprises at least 30% by weight of fructose.

4. The dry consumable preparation of claim 1, in the form of a pressed tablet or a powder encapsulated in a water-dissolvable capsule.

5. The dry consumable preparation of claim 1, wherein the preparation is a powder.

6. The dry consumable preparation of claim 1, wherein the preparation comprises between 0.05% and 0.3% by weight of cannabidiol (CBD) oil.

7. The dry consumable preparation of claim 6, comprising up to 0.155% by weight of CBD oil.

8. The dry consumable preparation of claim 6, comprising up to 0.15% by weight of CBD oil.

9. The dry consumable preparation of claim 1, wherein the bulking agent comprises fructose; and
   the preparation further comprises a nutraceutical composition, the nutraceutical composition comprising:
   Quillaja,
   one or more herbal extracts, and
   one or more nutrient vitamins or minerals.

10. The dry consumable preparation of claim 9, wherein the one or more herbal extracts includes at least one of cayenne extract, lemon oil, turmeric extract, cinnamon oil, bromelain, lavender oil, tart cherry, or passion flower extract.

11. The dry consumable preparation of claim 9, wherein the one or more herbal extracts includes an essential oil.

12. The dry consumable preparation of claim 9, wherein the one or more vitamins and minerals includes at least one of 1-theanine, vitamin C, Folic Acid, vitamin D, glucosamide sulfate, biotin, vitamins A, B1, B2, B3, B6, B12, and zinc gluconate.

13. A method of making a dry consumable preparation, the method comprising:
   mixing at least one of a cannabinoid or a cannabinoid extract containing one or more cannabinoids with a bulking agent, whereby the at least one of the cannabinoid or the cannabinoid extract containing one or more cannabinoids is plated onto the bulking agent; and
   introducing an effervescence agent to the mixture, the effervescence agent having sodium bicarbonate, potassium bicarbonate, and at least one acid, the at least one acid having at least one of citric acid, tartaric acid, or malic acid, wherein a weight ratio of the effervescence agent to the at least one acid ranges from 0.5:0.5 to 4.0:30.0, wherein the weight ratio is configured to create a chemical pH buffering system at a targeted pH range between 2 and 6 when the dry consumable preparation is added to a targeted amount of water.

* * * * *